United States Patent
Gläsel et al.

(10) Patent No.: US 10,549,486 B2
(45) Date of Patent: Feb. 4, 2020

(54) PROCESS FOR THE MANUFACTURE OF AN IMPERMEABLE CONNECTION BETWEEN AT LEAST TWO FLUID CARRYING SILICONE HOSE COMPONENTS AND A FLUID CARRYING ASSEMBLY MANUFACTURED ACCORDING TO SAID PROCESS

(71) Applicant: Raumedic AG, Münchberg (DE)

(72) Inventors: Björn Gläsel, Kirchenlamitz (DE); Jörg Prescher, Ramsthal (DE); Axel Wunderlich, Ebmath (DE); Robert Reichenberger, Wunsiedel (DE)

(73) Assignee: Raumedic AG, Münchberg (DE)

( * ) Notice: Subject to any disclaimer, the term of this patent is extended or adjusted under 35 U.S.C. 154(b) by 1205 days.

(21) Appl. No.: 14/828,798

(22) Filed: Aug. 18, 2015

(65) Prior Publication Data
US 2016/0046069 A1 Feb. 18, 2016

(30) Foreign Application Priority Data
Aug. 18, 2014 (DE) .......................... 10 2014 216 329

(51) Int. Cl.
*B29C 65/00* (2006.01)
*B29C 65/48* (2006.01)
(Continued)

(52) U.S. Cl.
CPC ....... *B29C 66/5221* (2013.01); *B29C 65/4835* (2013.01); *B29C 65/562* (2013.01);
(Continued)

(58) Field of Classification Search
CPC ....... F16L 13/10; F16L 13/103; F16L 13/106; F16L 13/11; F16L 13/113; F16L 13/116
See application file for complete search history.

(56) References Cited

U.S. PATENT DOCUMENTS

| 6,290,265 B1 * | 9/2001 | Warburton-Pitt | ....... F16L 47/02 |
| | | | 285/131.1 |
| 2008/0277926 A1 * | 11/2008 | Inman, Jr. | ............. A61M 39/10 |
| | | | 285/123.15 |
| 2016/0195208 A1 * | 7/2016 | Cassiday | ............... F16L 41/021 |
| | | | 285/125.1 |

FOREIGN PATENT DOCUMENTS

| WO | 2007048072 | 4/2007 |
| WO | 2009117059 | 9/2009 |
| WO | 2012163819 | 12/2012 |

OTHER PUBLICATIONS

European Patent Office, European Search Report for EP 15 18 0183, dated Jan. 25, 2016 (Year: 2016).*

* cited by examiner

*Primary Examiner* — James M Hewitt, II
(74) *Attorney, Agent, or Firm* — Boyle Fredrickson S.C.

(57) ABSTRACT

In a process for the manufacture of an impermeable connection between at least two fluid carrying silicone hose components, the silicone hose components and a silicone connector component are first prepared. Afterwards a fluid silicone mass is applied to at least one connecting area where the silicone hose components abut on the silicone connector components. The at least one connecting area is post cured to harden the silicone mass. In a fluid carrying assembly with at least two fluid carrying silicone hose components and at least one silicone connector component, a fluid carrying connection is manufactured between these components by means of this process. This design results in a connecting technique that is, on the one hand, secure and, on the other hand, enables automation of the manufacture of an impermeable connection and thus of the fluid carrying assembly.

6 Claims, 2 Drawing Sheets

(51) Int. Cl.
*B29C 65/56* (2006.01)
*F16L 11/00* (2006.01)
B29K 683/00 (2006.01)
B29L 23/00 (2006.01)

(52) U.S. Cl.
CPC ............ *B29C 66/71* (2013.01); *F16L 11/005* (2013.01); *B29K 2683/00* (2013.01); *B29L 2023/005* (2013.01)

PROCESS FOR THE MANUFACTURE OF AN IMPERMEABLE CONNECTION BETWEEN AT LEAST TWO FLUID CARRYING SILICONE HOSE COMPONENTS AND A FLUID CARRYING ASSEMBLY MANUFACTURED ACCORDING TO SAID PROCESS

CROSS-REFERENCES TO RELATED APPLICATIONS

This application claims the priority of German Patent Application, Serial no. 10 2014 216 329.3, filed Aug. 18, 2014, pursuant to 35 U.S.C. 119(a)-(d), the content of which is incorporated herein by reference in its entirety as if fully set forth herein.

FIELD OF THE INVENTION

This invention regards a process for the manufacture of an impermeable and more particularly a media-impermeable connection between at least two fluid carrying silicone hose components. The invention also concerns a fluid carrying assembly with at least two fluid carrying silicone hose components and at least one silicone connector component between which a fluid carrying connection is manufactured by means of a process of this kind.

BACKGROUND OF THE INVENTION

We are familiar with a fluid carrying assembly with several hose components and at least one connector component in patent WO 2012/163819 A2, which gives examples of connector component variants such as T connectors, L connectors, Y connectors and straight connectors. Further fluid carrying assemblies can be seen in patents WO 2009/117059 A2 and WO 2007/048072 A2.

SUMMARY OF THE INVENTION

It is an object of this invention to design a connecting technique that is, on the one hand, secure and, on the other hand, enables automation of the manufacture of an appropriately impermeable and particularly media-impermeable connection and thus a fluid carrying assembly.

According to the invention, this object is achieved through a manufacturing process of an impermeable connection between at least two fluid carrying hose components with the following steps:
provision of the silicone hose components and a silicone connector component;
application of a fluid silicone mass to at least one connecting area where the silicone hose components abut on the silicone connector component;
polymeric post curing of at least one connecting area to harden the silicone mass.

Silicone/a silicone connection is manufactured, according to the manufacturing process included in the invention. Polymeric post curing results in a deep material connection of the silicone components connected via the silicone mass, possessing the characteristics of a connection made up of a single piece. Contact between the at least one silicone hose component and the silicone connector component may take place before or after application of the silicone mass. If contact takes place before application of the silicone mass, penetration of the silicone mass into the fluid carrying channel of the fluid carrying assembly can be avoided. A silicone connector component may be joined to between two to six silicone hose components, depending on the design of the connector component. A connecting area may either serve to connect the silicone connector component to exactly one silicone connector component or also serve to join exactly one connector component with more than one hose component. The connector components and/or the hose components may be manufactured as injection molded parts. The impermeable or fluid-tight connection manufactured may also be impermeable to other media, particularly to solids. Polymeric post curing of the connecting area may take place through annealing. By annealing the connecting junctions, the connecting junctions are heated for a certain period of time without deforming the silicone mass so that the silicone mass is hardened. Polymeric post curing may alternatively or additionally also be initiated through different determining factors, such as UV light radiation and/or targeted changes to humidity, and particularly by increased targeted changes to humidity. Annealing may take place over a period of time ranging from 10 minutes to 5 hours, and in particular over a period of time ranging from 30 minutes to 2 hours. The temperature for annealing may range from 80° C. to 200° C., and in particular from 150° C. to 200° C.

During application of the silicone mass to the connecting area, this one defined tensile force may be exerted on the silicone mass. This results in internal tension and stretching of the applied silicone mass, favoring post curing at a later stage.

Pre-hardening of the silicone mass may be carried out by heat treatment and in particular by infrared radiation. Pre-hardening may result in post curing of the silicone mass. Pre-hardening results in pre-positioning, i.e. the fixing of the silicone mass prior to the actual post curing of the polymers. This facilitates handling of the connecting area during the manufacturing process.

In order to bring at least one of the silicone hose components into contact with the silicone connector component in the connecting area, both components are pushed inside each other, which results in secure connection of the components.

Pushing of the components inside each other results in pre-centering of the silicone hose component relative to the silicone connector component, which avoids undesirable radial displacement of the components to be connected and prevents the creation of undesirable dead spaces. Moreover, the assembly with at least one connector component and the hose components may be prefabricated and, at a later stage, finally connected with the aid of the silicone mass.

Application of the silicone mass externally to the connecting area results in the simple manufacture of the impermeable connection.

During application the silicone mass is applied to an externally covered collection zone of the connecting area. This introduction of the silicone mass avoids the hardened silicone mass being visible in the manufactured product. Uniform appearance may thus be guaranteed. Introduction of the silicone mass into the collection zone may take place through predefined introductory channels. The collection zone and/or at least one introductory channel may be designed so that an exactly prescribed amount of silicone mass may be used for the connecting process. A sheath to cover the collection zone may further improve the appearance of the connecting area.

Expansion of the sheath to cover the collection zone, before bringing it into contact with the at least one silicone hose component on the silicion connector component, enables the introduction of the fluid silicone mass through an introductory channel temporarily made available by the sheath. Expansion of the sheath may take place mechanically or chemically. Expansion may take place prior to sliding the components inside each other.

The advantages of a fluid carrying assembly with at least two fluid carrying silicone hose components and at least one silicone connector component between which a fluid carrying connection is manufactured according to the invention correspond to those already explained above with reference to the manufacturing process.

Silicone hose components and the silicone connector component being made from the same silicone material composition, particularly facilitate accreditation of the fluid carrying assembly in the field of technology-based medicine. The fluid silicone mass may also consist of the same silicone material composition as the silicone connector component and/or the silicone hose components.

The advantages of the sheath covering at least one collection zone of a connecting area where the silicone hose components abut on the silicone connector component, and completely closing the collection zone externally have already been explained with reference to the manufacturing process.

Depending on the design of the fluid carrying assembly, exactly one introductory channel to one of the components for insertion of the silicone mass in the collection zone externally through these components may be provided or there may be several more, for example two to five introductory channels. The at least one introductory channel may move radially to a hose axis or to a longitudinal axis of the components. Several introductory channels may likewise be designed for peripheral distribution around this hose axis. The at least one introductory channel may be designed in the connector.

Pre-centering of the hose components relative to the connector components may be guaranteed by a centering device in the connecting area.

Exemplary embodiments of the invention will now be explained in greater detail with reference to the drawing:

DESCRIPTION OF THE PREFERRED EMBODIMENTS

Figure 1:
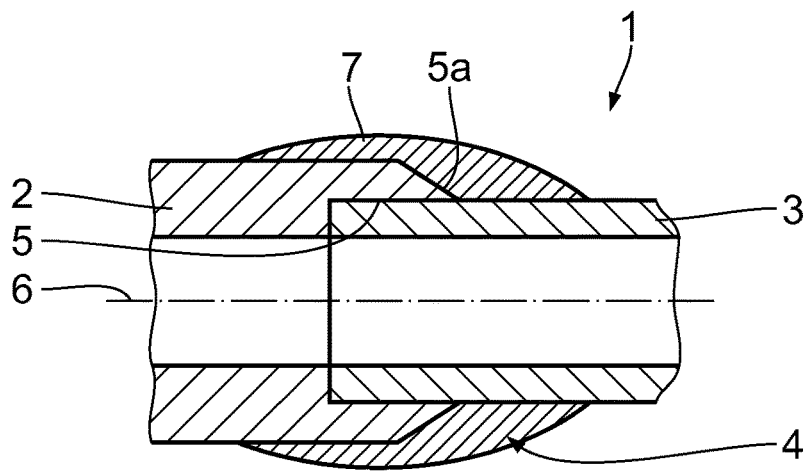
FIG. 1 shows a longitudinal section through a sectional view of a fluid carrying assembly, whereby there is a connecting area between a silicone connector component and a silicone hose component.

FIG. 1 shows a longitudinal section of a connecting area of a fluid carrying assembly 1. The fluid carrying assembly 1 is for use in medical applications. Examples of such applications are included in patent WO 2012/163819 A2 and the references quoted in this patent. Detailed reference will be made to this publication in the following description.

Apart from at least one silicone connector component, the fluid carrying assembly 1 has 2 further silicone hose components; exactly one of these silicone hose components 3 is shown in FIG. 1. The hose components 3 are connected via the connector components 2. The connector components 2 may be designed as T connectors, L connectors, Y connectors and even straight connectors. Two or three hose components 3 may thus be connected via a connector component 2. In principle, even more hose components may be connected via a connector component, for example four, five or six hose components.

Both the connector components 2, on the one hand, and the hose components 3, on the other hand, may be made of the same silicone material composition.

In the connecting area 4 of the fluid carrying assembly 1, where the hose component 3 is connected to the connector component 2, the connector component 2 has a centering device 5. With reference to a longitudinal axis 6 of the connecting area 4, the centering device forms centered collection of the connector component 2 that the hose component 3 is pushed into. A leading front wall 5a of the connector component 2, facing the hose component 3, is conically designed to taper off to an external circumferential wall of the hose component 3. This favors a tight closing between the connector component 2 and the hose component 3 in the connecting area 4.

A hardened silicone mass 7, previously applied as a raw fluid mass to the connecting area 4, serves for the impermeable connection of the connector component 2 to the hose component 3. In order to harden the silicone mass 7, it was post cured after application to the connecting area 4.

For manufacture of the impermeable connection in the connecting area 4, the hose component 3 may either first be pushed inside the connector component 2 and afterwards transferred to the still fluid silicone mass 7, or the procedure may be reversed, whereby the silicone mass is first prepared for transfer to the connector component 2 and/or the hose component 3 in the connecting area 4, and afterwards the hose component 3 is pushed inside the connector component 2.

In a manufacturing process that is not shown, the hose component may even hold the centering device in which, in this case, the connector component is pushed inside.

In the design shown in FIG. 1, the connecting area 4 serves to connect the connector component 2 to exactly one hose component 3. In a variant of the design that is not shown, the connecting area 4 may also serve to connect the connector component to several hose components.

The silicone mass 7 may consist of a high-temperature vulcanized (HTV) silicone, a liquid silicone rubber (LSR), a silicone adhesive or even a different kind of silicone.

For manufacture of the impermeable connection between at least two fluid carrying silicone hose components like hose component 3, the silicone hose component and at least one silicone connector component are first prepared, for example like connector component 2. Afterwards the fluid silicone mass 7 is applied to at least one connecting area 4 where the silicone hose component 3 is lying on the silicone connector component 2. Thus the at least one connecting area 4 is post cured to harden the silicone mass 7.

Prior to application to the connecting area 4, the fluid silicone mass 7 may be prepared. In this process, a raw silicone mass is first rolled so that a preform may be produced from the rolled raw silicone mass, for example a tube of a prescribed diameter. A tube of this kind may be produced through extrusion. Alternatively, instead of a tube, a pre-form may be produced in the form of a strip or profile, particularly through extrusion. What is more, a tube shaped pre-form of the raw silicone mass may be rolled flat between two sheets. These sheets may be fluted or tufted, thus making it easier for the pre-form to be removed from the sheets surrounding it after rolling After removal, the silicone mass rolled between the sheets is ready to be applied to the connecting area 4.

When the fluid silicone mass 7 is applied to the connecting area, it may be stretched. This may be done by exerting tensile stress on the silicone mass during application.

Prior to polymeric post curing, and particularly before annealing, the silicone mass 7 may be pre-hardened. This pre-hardening may be carried out through exposing the applied silicone mass to infrared light radiation. Pre-hardening serves to post cure the silicone mass 7 and/or to pre-position or fix the silicone mass 7 prior to the actual post curing process.

In order to bring the hose component 3 into contact with the connector component 2, which may take place before or after application of the silicone mass 7, according to the design in FIG. 1, the hose component 3 is pushed into the centering device 5 of the connector component 2.

In the design in FIG. 1, the silicone mass is applied externally to the connecting area 4. The silicone mass 7 completely seals the connecting area around the longitudinal axis 6.

Further designs of fluid carrying assemblies will now be discussed with reference to FIGS. 2 to 6. Any components corresponding to those that have already been explained with reference to other figures will not be re-discussed in any detail.

Figure 2:
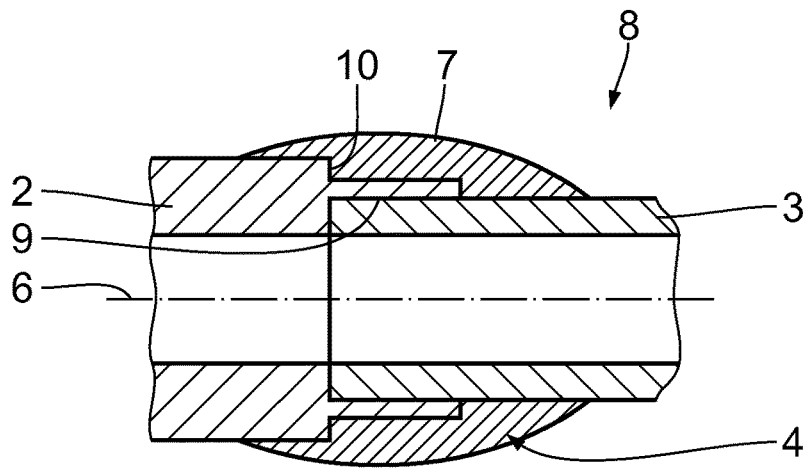
FIGS. 2 to 6 each shows further designs of a connecting area of a fluid carrying assembly, in a similar way to FIG. 1.

The fluid carrying assembly 8 in FIG. 2 has a centering device 9 in the form of a centering sleeve that is part of the connector component 2, and is shaped on a front wall 10 of the connector component 2. At the height of the centering device 9, an external circumference of the connector component 2 also becomes narrower in steps. In the connecting area 4 of the fluid carrying assembly 8, there are thus several rectangular step transitions making it easier for the silicone mass 7 to adhere.

Figure 3:
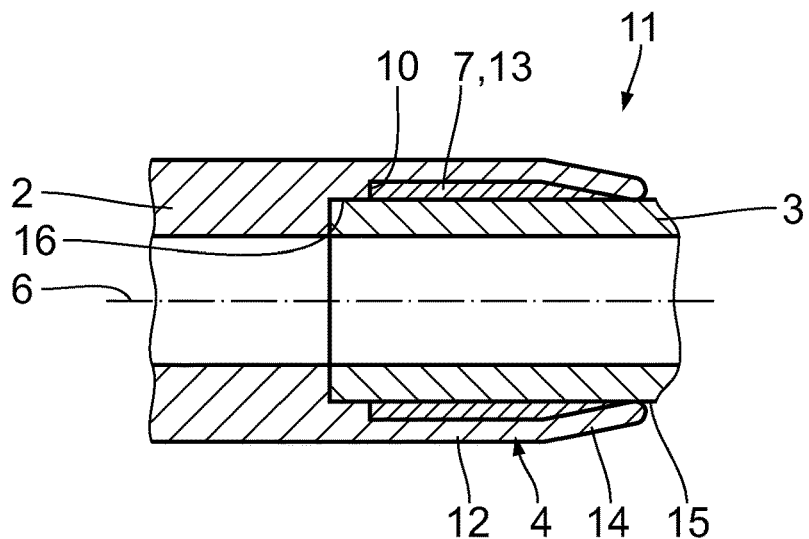

In fluid carrying assembly 11 in FIG. 3, the connector component 2 has a sheath 12 to cover a collection zone 13 of the connecting area 4, where the hose component 3 abuts on and comes in contact with the connector component 2. The collection zone 13 is designed as an external annular zone surrounding the hose component 3, completely extending around the longitudinal axis 6.

The sheath 12 is designed as a sheath sleeve whose external circumference first corresponds to the external circumference of the connector component 2, whereby the sheath 12 tapers off conically in the area of a free end 14, so that the sheath 12 on the free end 14 abuts directly on an external cladding wall 15 of the hose component 3. The collection zone is thus closed on all sides. In the design in FIG. 3, the silicone mass 7 is in the collection zone 13, thus filling it. The silicone mass 7 is taken to the collection zone 13, either before or after the hose component 3 is pushed into the connector component 2.

In the design in FIG. 3, the connector component 2 also has a centering device 16 for the hose component 3, which is designed as a circumferential step in the front wall 10 of the connector component 2.

When the fluid silicone mass 7 is applied to the connecting component 2, after being pushed into the hose component 3, the silicone mass 7 is, for example, injected between the free end 14 and the cladding wall 15. Alternatively, injection may also be carried out through an insertion channel (this is not shown in greater detail) constituting a fluid connection between the collection zone and an external surrounding of the fluid carrying assembly 11. The insertion channel may run radially and/or axially in relation to the longitudinal axis 6. Several insertion channels may be available. For example, there may even be two, three, four, five or more insertion channels available. The insertion channels may be positioned, equally distributed in a circumferential direction around the longitudinal axis.

For manufacture of the impermeable connection, the silicone mass 7 is applied to the externally covered collection zone 13 of the connecting area 4.

The at least one insertion channel may be designed in the connector component 2.

Alternatively or additionally, the external connector component 2 may be spread into the connecting area 4 with the aid of a spreading device so that the internal hose component 3, with the previously applied silicone mass 7, may be pushed into the connecting area 7 that was first spread, without the external side of the silicone mass 7 coming into contact with the internal wall of the connector component 2 in the connecting area 4, in the process. After the hose component 3 has been pushed into the connector component, the spreading process may be ended, so that the silicone mass 7 is radially internal to the hose component 5 and radially external from the connector component in the connecting area. Polymeric post curing may then follow to harden the silicone mass 7. During this process the connecting area may, for example, be annealed at 200° C. for a period of two hours.

Figure 4:
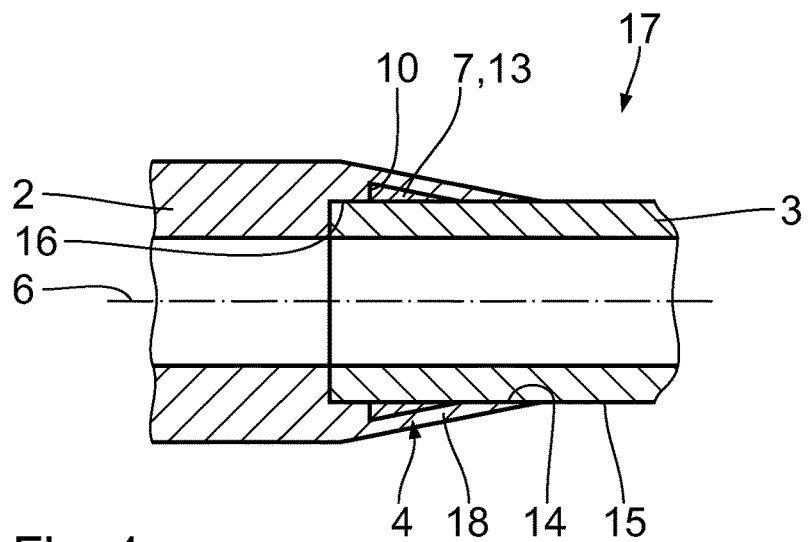

The design of the fluid carrying assembly 17 in FIG. 4, has a sheath 18 whose function and design correspond to that of sheath 12 in FIG. 3, tapering off conically. In turn, the sheath 18 runs away from the front wall 10, abuts over its free end 14 via a two-dimensional surface area on the cladding wall 15 of the hose component 3. In the design in FIG. 4 the collection zone 13 has a triangular annular cross section.

Before the hose component 3 is brought into contact with the connector component 2, the sheath 12 or sheath 18 may be expanded.

Figure 5:
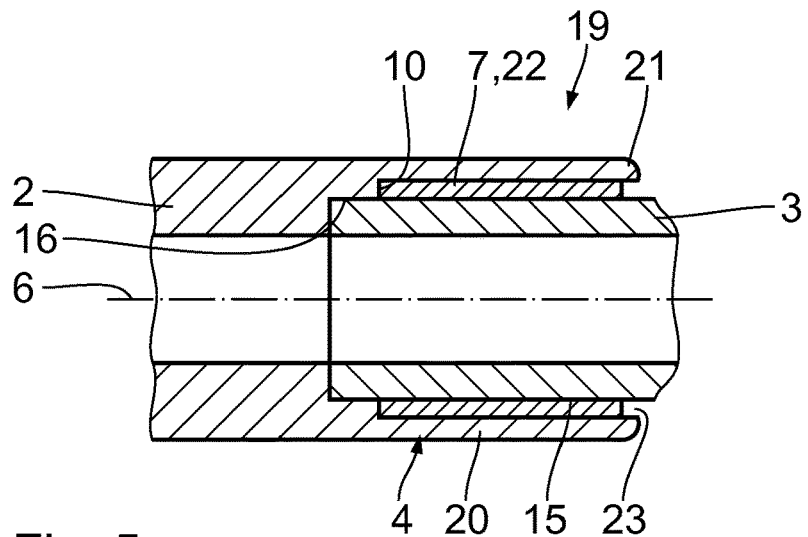

FIG. 5 shows a further design of the fluid carrying assembly 19. A sheath 20 in fluid carrying assembly 19 differs from the sheath 12 in the design shown in FIG. 3 in that at its free end 21, the sheath 20 does not abut on the external cladding wall 15 of the hose component 3. In the design in FIG. 5 a collection zone 22 for the silicone mass 7 is thus not closed on all sides, because an annular opening 23 remains between the free end 21 and the cladding wall 15, enabling external access to the collection zone 22.

Figure 6:
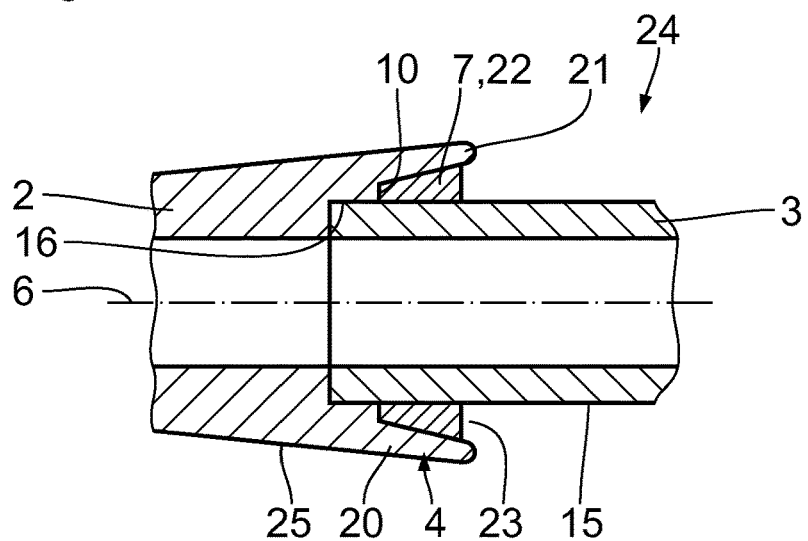

FIG. 6 shows a further design of the fluid carrying assembly 24 with a sheath 20 and a collection zone 22 with external access. Unlike the design shown in FIG. 5, the collection zone 22 conically expands to the annular opening 23. This corresponds to a conical expansion of an external cladding wall 25 of the connector component that is passed to the sheath 20 in the connecting area 4.

What is claimed is:

1. A process for the manufacture of an impermeable connection between at least two fluid carrying hose components comprising:
   provision of a plurality of fluid carrying silicone hose components and a silicone connector component;
   application of a fluid silicone mass to at least one connecting area where the silicone hose components abut on the silicone connector component; and
   polymeric post curing of at least one connecting area to harden the silicone mass;
wherein the silicone connector component has a sheath to externally cover a collection zone of the at least one connecting area; and wherein during application of the fluid silicone mass, the fluid silicone mass is applied to the collection zone of the at least one connecting area that is externally covered by the sheath.

2. The process according to claim 1, wherein pre-hardening of the silicone mass takes place prior to post curing.

3. The process according to claim 1, wherein in order to bring at least one of the silicone hose components into contact with the silicone connector component in the connecting area, the at least one of the silicone hose components is pushed inside the silicone connector component.

4. The process according to claim 3, wherein pushing of the at least one of the silicone hose components inside the silicone connector component results in pre-centering of the at least one of the silicone hose components relative to the silicone connector component.

5. The process according to claim 1, wherein the sheath is expanded before being brought into contact with at least one of the silicone hose components.

6. The process according to claim 1, wherein polymeric post curing of the connecting area takes place through annealing.

* * * * *